(12) United States Patent
Zhu et al.

(10) Patent No.: US 7,062,314 B2
(45) Date of Patent: Jun. 13, 2006

(54) CARDIAC RHYTHM MANAGEMENT DEVICE WITH TRIGGERED DIAGNOSTIC MODE

(75) Inventors: Qingsheng Zhu, Little Canada, MN (US); Julio C. Spinelli, Shoreview, MN (US); Bruce H. KenKnight, Maple Grove, MN (US); Gerrard M. Carlson, Champlin, MN (US)

(73) Assignee: Cardiac Pacemakers, Inc., Saint Paul, MN (US)

( * ) Notice: Subject to any disclaimer, the term of this patent is extended or adjusted under 35 U.S.C. 154(b) by 762 days.

(21) Appl. No.: 10/035,009

(22) Filed: Dec. 28, 2001

(65) Prior Publication Data

US 2002/0120306 A1 Aug. 29, 2002

Related U.S. Application Data

(63) Continuation-in-part of application No. 09/850,537, filed on May 7, 2001, which is a division of application No. 09/411,345, filed on Oct. 1, 1999, now Pat. No. 6,272,377, application No. 10/035,009, which is a continuation-in-part of application No. 09/802,316, filed on Mar. 8, 2001.

(51) Int. Cl.
*A61B 5/0468* (2006.01)

(52) U.S. Cl. ...................................................... 600/515
(58) Field of Classification Search ................. 600/508, 600/509, 513–518, 521, 300; 607/4, 5, 9, 607/14, 28
See application file for complete search history.

(56) References Cited

U.S. PATENT DOCUMENTS

| | | | |
|---|---|---|---|
| 4,872,459 A | 10/1989 | Pless et al. | 128/419 |
| 4,880,005 A | 11/1989 | Pless et al. | 128/419 PG |
| 5,291,400 A | 3/1994 | Gilham | 364/413.06 |
| 5,447,519 A | 9/1995 | Peterson | 607/5 |
| 5,466,245 A | 11/1995 | Spinelli et al. | 607/17 |
| 5,560,370 A | 10/1996 | Verrier et al. | 128/705 |
| 5,603,331 A | 2/1997 | Heemels et al. | 128/696 |
| 5,645,570 A | 7/1997 | Corbucci | 607/5 |
| 5,682,901 A | 11/1997 | Kamen | 128/706 |
| 5,749,900 A | 5/1998 | Schroeppel et al. | 607/4 |

(Continued)

FOREIGN PATENT DOCUMENTS

| | | |
|---|---|---|
| EP | 0709112 | 5/1996 |
| WO | WO-94/06350 | 3/1994 |
| WO | WO-98/15319 | 4/1999 |
| WO | WO-00/04950 | 2/2000 |
| WO | WO-00/38782 | 7/2000 |
| WO | WO-00/44274 | 8/2000 |
| WO | WO-00/51680 | 9/2000 |

OTHER PUBLICATIONS

"Heart Rate Variability: Standards of Measurement, Physiological Intrepretation, and Clinical Use", *European Heart Journal, 17,* Prepared by the Task Force of The European Society of Cardiology and The North American Society of Pacing and Electrophysiology; published by the American Heart Association, Inc.; European Society of Cardiology, (1996),pp. 354–381.

(Continued)

*Primary Examiner*—George Manuel
(74) *Attorney, Agent, or Firm*—Schwegman, Lundberg, Woessner & Kluth, P.A.

(57) ABSTRACT

A device and method in which spectral analysis of heart rate variability is performed in order to assess autonomic balance. When a threshold level is reached, a diagnostic mode is triggered in which the device performs computationally intensive data analysis to assess the probability of a pathological event such as an arrhythmia occurring.

20 Claims, 3 Drawing Sheets

U.S. PATENT DOCUMENTS

| | | | |
|---|---|---|---|
| 5,755,671 A | 5/1998 | Albrecht et al. | 600/516 |
| 5,842,997 A | 12/1998 | Verrier et al. | 600/518 |
| 5,861,013 A * | 1/1999 | Peck et al. | 607/28 |
| 5,891,044 A | 4/1999 | Golosarsky et al. | 600/509 |
| 5,893,882 A | 4/1999 | Peterson et al. | 607/14 |
| 5,921,940 A | 7/1999 | Verrier et al. | 600/518 |
| 5,941,831 A | 8/1999 | Turcott | 600/515 |
| 6,021,351 A | 2/2000 | Kadhiresan et al. | 607/19 |
| 6,026,320 A | 2/2000 | Carlson et al. | 600/510 |
| 6,035,233 A | 3/2000 | Schroeppel et al. | 600/515 |
| 6,042,548 A | 3/2000 | Giuffre | 600/483 |
| 6,135,970 A | 10/2000 | Kadhiresan et al. | 600/595 |
| 6,144,878 A | 11/2000 | Schroeppel et al. | 600/515 |
| 6,216,032 B1 | 4/2001 | Griffin et al. | 600/515 |
| 6,224,553 B1 | 5/2001 | Nevo | 600/437 |
| 6,246,909 B1 | 6/2001 | Ekwall | 607/9 |
| 6,269,263 B1 | 7/2001 | Ohnishi et al. | 600/518 |
| 6,272,377 B1 | 8/2001 | Sweeney et al. | 600/515 |
| 6,358,201 B1 | 3/2002 | Childre et al. | 600/300 |
| 6,390,986 B1 | 5/2002 | Curcie et al. | 600/485 |
| 6,438,421 B1 | 8/2002 | Stahmann et al. | 607/9 |
| 6,453,201 B1 | 9/2002 | Daum et al. | 607/62 |
| 6,470,210 B1 | 10/2002 | Chen et al. | 600/515 |
| 6,480,733 B1 | 11/2002 | Turcott | 600/516 |
| 6,480,742 B1 | 11/2002 | Stahmann et al. | 607/27 |
| 6,571,121 B1 | 5/2003 | Schroeppel et al. | 600/515 |
| 6,571,122 B1 | 5/2003 | Schroeppel et al. | 600/515 |
| 6,668,194 B1 | 12/2003 | VanHout | 607/9 |
| 6,678,547 B1 | 1/2004 | Carlson et al. | 600/515 |
| 2002/0016550 A1 | 2/2002 | Sweeney et al. | 600/515 |
| 2002/0029000 A1 | 3/2002 | Ohsaki | 600/500 |
| 2002/0072683 A1 | 6/2002 | Schroeppel et al. | 600/515 |
| 2002/0082509 A1 | 6/2002 | Vanderlinde et al. | 600/510 |
| 2003/0060851 A1 | 3/2003 | Kramer et al. | 607/9 |
| 2003/0097155 A1 | 5/2003 | Stahmann et al. | 607/9 |

OTHER PUBLICATIONS

"Heart Rate Variability: Standards of Measurement, Physiological Interpretation, and Clinical Use", *Circulation, 93,* (1996),pp. 1043–1065.

Behrens, S., et al., "Effects of Amiodarone on the Circadian Pattern of Sudden Cardiac Death (Department of Vererans Affairs Congestive Heart Failure–Survival Trial of Antiarrhythmic Therapy)", *Am. J. Cardiol., 80(1),* (Jul. 1997), 45–48.

Behrens, S., et al., "Modification of the Circadian Pattern of Ventricular Tachyarrhythmias by Beta–Blocker Therapy", *Clin. Cardiol. 20(3),* (Mar. 1997),253–257.

Berger, R. D., et al., "An Efficient Algorithm for Spectral Analysis of Heart Rate Variability", *IEEE Transactions on Biomedical Engineering,* BME–33 (9), (Sep. 1986),900–904.

Bigger, J. T., et al., "Correlations Among Time and Frequency Domain Measures of Heart Period Variability Two Weeks After Acute Myocardial Infraction", *Arrhythmias and Conduction Disturbances, 69,* (Apr. 1, 1992),891–898.

Bigger, Jr., J. T., "Spectral Analysis of R–R Variability to Evalute Autonomic Physiology and Pharmacology and to Predict Cardiovascular Outcomes in Humans", *Am. J. Cardiol.,69(9),* (Apr. 1, 1992),891–898.

Bocker, D., et al., "Ventricular Resynchronization Therapy May Restore Autonomic Balance as Evidenced by Redicung the Low Frequency to High Frequency Autonomic Ratio in Heart Failure Patients", *4th International Meeting organized by the Working Group on Heart Failure of the European Society of Cardiology(Abstract),* Barcelona, Spain,(Jun. 11, 2001),1 p.

Crawford, Michael H., et al., "ACC/AHA Guidelines for Ambulatory Electrocardiography", *JACC, vol. 34, No. 3,* Published by Elsevier Science Inc., (Sep. 1999),912–948.

Dyjach, John A., et al., "Method for Exclusion of Ectopic Events from Heart Rate Variability Metrics", U.S. Appl. No. 10/728,124, filed Dec. 4, 2003, 21 pgs.

Hayano, J., et al., "Circadian Rhythms of Atrioventricular Conduction Properties in Chronic Atrial Fibrillation With and Without Heart Failure", *JACC,* 31 (1), (Jan. 1998),pp. 158–166.

Lavery, C. E., et al., "Nonuniform Nighttime Distribution of Acute Cardiac Events", *Circulation,*96 (10), (Nov. 18, 1997),pp. 3321–3327.

Peckova, M., et al., "Circadian Variations in the Occurence of Cardiac Arrests", *Circulation,*98 (1), (1998),pp. 31–39.

Yamashita, T., et al., "Circadian Variation of Paroxysmal Atrial Fibrillation", *Circulation, 96 (5),* (Sep. 2, 1997),pp. 1537–1541.

* cited by examiner

CARDIAC RHYTHM MANAGEMENT DEVICE WITH TRIGGERED DIAGNOSTIC MODE

RELATED APPLICATIONS

This application is a continuation-in-part of U.S. patent application Ser. No. 09/850,537, filed May 7, 2001, entitled "Cardiac Rhythm Management System with Arrhythmia Prediction and Prevention," which is a division of U.S. patent application Ser. No. 09/411,345, filed Oct. 1, 1999, now issued as U.S. Pat. No. 6,272,377, and U.S. patent application Ser. No. 09/802,316, filed Mar. 8, 2001, entitled "Cardiac Rhythm Management System Using Time-Domain Heart Rate Variability Indicia," the disclosures of which are hereby incorporated by reference in their entirety.

FIELD OF THE INVENTION

This invention pertains to methods and apparatus for cardiac rhythm management, which includes the treatment of arrhythmias and the acquisition of diagnostic data.

BACKGROUND

Cardiac rhythm management devices are implantable devices that provide electrical stimulation to selected chambers of the heart in order to treat disorders of cardiac rhythm. Such devices include pacemakers and implantable cardioverter/defibrillators as well as devices with both types of functionality. Cardiac rhythm management devices have the capability of sensing the intrinsic activity of the heart in order to both deliver certain types of pacing and to detect pathological conditions. Certain devices also have sensors for sensing other physiological variables such as respiratory rate and stroke volume. These devices also have sufficient processing power to perform sophisticated analysis of the data collected by its sensors for the purpose of predicting the occurrence of pathological events, such as an arrhythmia. If such an event is predicted to occur, the device can deliver appropriate therapy and/or alert the patient or clinical personnel. Because implantable devices have limited processing power and are powered by a battery, replacement of which requires re-implantation, it is not practical for a device to continuously perform computation intensive data analysis. It would be useful, therefore, if the device could identify situations where such data analysis would be warranted.

SUMMARY OF THE INVENTION

Increased activity of the sympathetic nervous system is associated with metabolic stress and may predispose a susceptible patient to the onset of a cardiac arrhythmia. If increased sympathetic activity could be detected in a patient in whom a cardiac rhythm management device is implanted, a diagnostic mode could then be triggered in which the device performs computationally intensive data analysis to assess the probability of the arrhythmia occurring. It has been found that spectral analysis of heart rate variability can be used to determine the level of sympathetic activity in a subject. Heart rate variability refers to the changes in heart rate that occur during a sinus rhythm (i.e., with normally activated and conducted heartbeats) and is primarily due to the interaction of the sympathetic and parasympathetic nervous systems. Low frequency variation in heart rate is due to both parasympathetic (or vagal) and sympathetic activity, while high frequency variation is primarily due to only parasympathetic activity. The ratio of low frequency variation to high frequency variation can thus be used as an indicator of the level of autonomic balance.

A cardiac rhythm management device can be programmed to measure and collect the time intervals between successive ventricular senses, referred to as RR intervals, for a period of time or a specified number of beats. The resulting series of RR interval values is then stored as a discrete signal and either used directly as indexed by heartbeat or resampled at a specified sampling frequency in order to equalize the time intervals. The RR interval signal can then be analyzed to determine its energies in the high and low frequency bands as described above. Although spectral analysis of an RR interval signal can be performed directly in the frequency domain, a time-domain technique for determining the signal power in defined high and low frequency bands is preferably used for reasons of computational economy. If the ratio of low frequency power to high frequency power exceeds a predetermined threshold value, a diagnostic mode in the device is triggered.

The above summary is intended to provide an overview of the subject matter of the present patent application. It is not intended to provide an exhaustive or exclusive explanation of the invention.

DETAILED DESCRIPTION

The present invention relates to a method for triggering a diagnostic mode in a cardiac rhythm management device. What follows is a description of the method as well as of the hardware components and operating modes of a device in which the method may be implemented.

1. Hardware Platform

In the embodiment to be described, the invention is implemented with a controller made up of a microprocessor executing programmed instructions in memory. It should be appreciated, however, that certain functions of a cardiac rhythm management device could be controlled by custom logic circuitry either in addition to or instead of a programmed microprocessor. The term "circuitry" as used herein should therefore be taken to encompass either custom circuitry (i.e., dedicated hardware) or a microprocessor-based controller executing programmed instructions contained in a processor-readable storage medium.

Pacemakers and other types of implantable cardiac rhythm management devices are typically implanted subcutaneously or submuscularly in a patient's chest and have leads threaded intravenously into the heart to connect the device to electrodes used for sensing and pacing. Leads may also be positioned on the epicardium by various means. A programmable electronic controller causes the pacing pulses to be output in response to lapsed time intervals and sensed electrical activity (i.e., intrinsic heart beats not as a result of a pacing pulse). Pacemakers sense intrinsic cardiac electrical activity by means of internal electrodes disposed near the chamber to be sensed. A depolarization wave associated with an intrinsic contraction of the atria or ventricles that is detected by the pacemaker and exceeds a specified threshold is referred to as an atrial sense or ventricular sense, respectively. In order to cause such a contraction in the absence of an intrinsic beat, a pacing pulse (either an atrial pace or a ventricular pace) with energy above a certain pacing threshold is delivered to a heart chamber.

Figure 1:
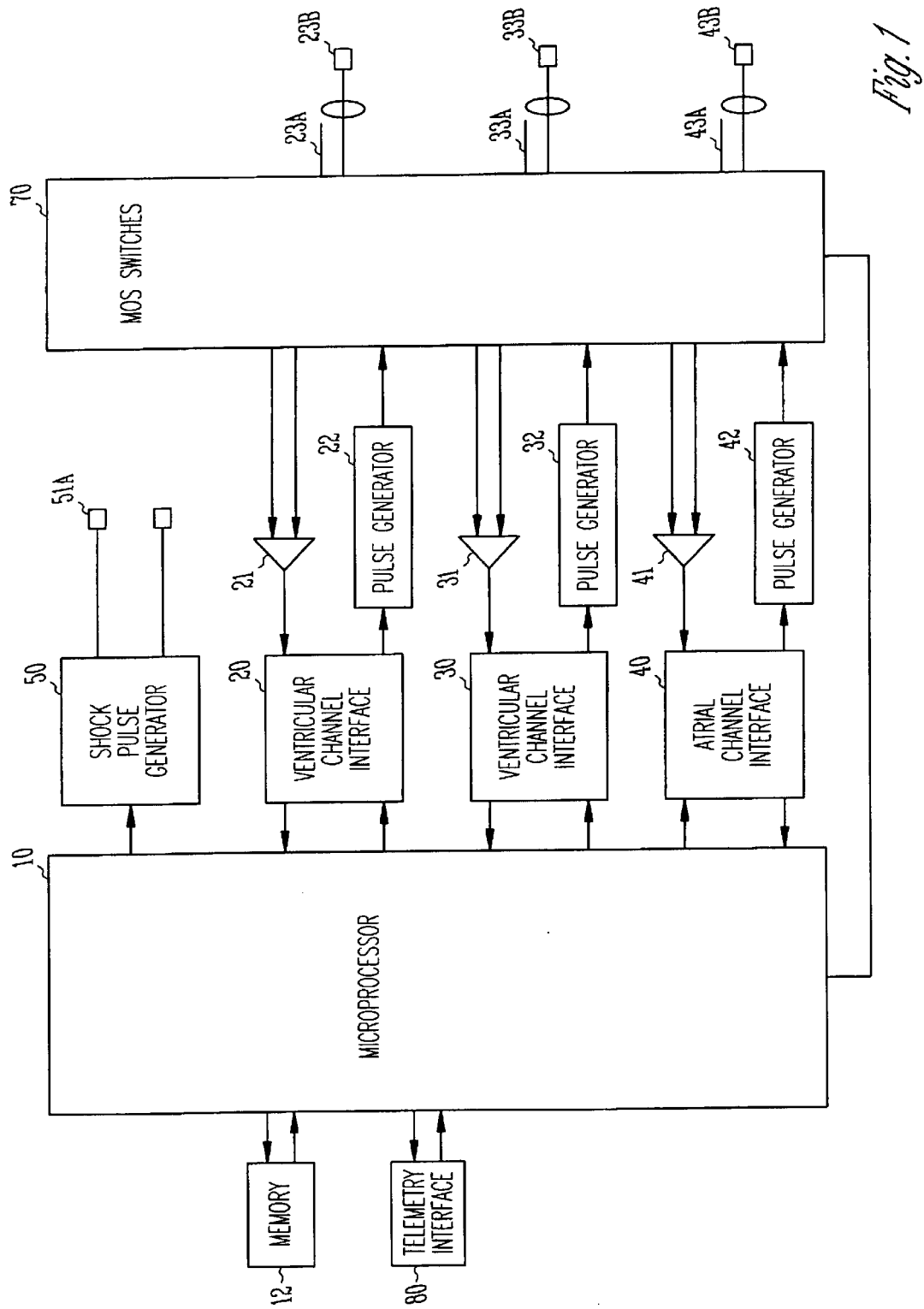
FIG. 1 is a system diagram of a pacemaker configurable for delivering resynchronization therapy.

A block diagram of a multi-site pacemaker having three sensing/pacing channels is shown in FIG. 1. (As the term is used herein, a "pacemaker" should be taken to mean any cardiac rhythm management device, such as an implantable cardioverter/defibrillator, with a pacing functionality.) The controller of the pacemaker is made up of a microprocessor 10 communicating with a memory 12 via a bidirectional data bus, where the memory 12 typically comprises a ROM (read-only memory) for program storage and a RAM (random-access memory) for data storage. The controller could be implemented by other types of logic circuitry (e.g., discrete components or programmable logic arrays) using a state machine type of design, but a microprocessor-based system is preferable. The controller is capable of operating the pacemaker in a number of programmed modes where a programmed mode defines how pacing pulses are output in response to sensed events and expiration of time intervals. A telemetry interface 80 is also provided for communicating with an external programmer.

The multiple sensing/pacing channels may be configured to deliver biventricular pacing, biatrial pacing, or multi-site pacing of a single chamber. Illustrated in FIG. 1 is a configuration with one atrial and two ventricular sensing/pacing channels for delivering biventricular pacing. The atrial sensing/pacing channel in FIG. 1 comprises ring electrode 43a, tip electrode 43b, sense amplifier 41, pulse generator 42, and an atrial channel interface 40 which communicates bidirectionally with a port of microprocessor 10. The device also has two ventricular sensing/pacing channels that similarly include ring electrodes 23a and 33a, tip electrodes 23b and 33b, sense amplifiers 21 and 31, pulse generators 22 and 32, and ventricular channel interfaces 20 and 30. Incorporated into each sensing/pacing channel is thus a pacing channel made up of the pulse generator connected to the electrode and a sensing channel made up of the sense amplifier connected to the electrode. The channel interfaces include analog-to-digital converters for digitizing signal inputs from the sensing amplifiers, registers that can be written to for adjusting the gain and threshold values of the sensing amplifiers, and registers for controlling the output of pacing pulses and/or changing the pacing pulse amplitude. For each channel, the same electrode pair is used for both sensing and pacing. In this embodiment, bipolar leads that include two electrodes are used for outputting a pacing pulse and/or sensing intrinsic activity. Other embodiments may employ a single electrode for sensing and pacing in each channel, known as a unipolar lead. A MOS switching network 70 controlled by the microprocessor is used to switch the electrodes from the input of a sense amplifier to the output of a pulse generator.

The controller 10 controls the overall operation of the device in accordance with programmed instructions stored in memory and with information derived from the sensing channels. The voltages sensed by the sensing electrodes are electrogram signals that are analogous to a surface ECG and provide a temporal record of cardiac depolarization and repolarization that occurs during either intrinsic or paced beats. The sensing circuitry of the pacemaker generates atrial and ventricular senses when voltages sensed by the electrodes of a particular channel exceed a specified threshold. A ventricular sense would correspond to an R wave on an ECG, and an atrial sense would correspond to a P wave. The controller 10 interprets sense signals from the sensing channels in order to detect arrhythmias and to control the delivery of paces in accordance with a pacing algorithm that employs such senses to trigger or inhibit pacing.

When an arrhythmia is detected, the controller may cause appropriate therapy to be delivered. For this purpose, the device in FIG. 1 also includes a shock pulse generator 50 interfaced to the controller for delivering cardioversion/defibrillation shocks to the heart via a pair of electrodes 51a and 51b. The device may also deliver pacing therapy in accordance with an anti-tachycardia pacing (ATP) protocol in order to treat certain arrhythmias as described below.

2. Operating Modes and Configurations

The device illustrated in FIG. 1 may be configured to deliver pacing pulses to selected heart chambers with any of its available pacing channels by appropriate disposition of the lead and electrodes associated with the channel. Once the leads are so disposed, selected pacing channels may be employed to deliver pacing therapy to selected pacing sites, referred to herein as a pacing configuration. As detailed below, such pacing therapy may be delivered in accordance with a number of different pacing modes.

Bradycardia pacing modes refer to pacing algorithms used to pace the atria and/or ventricles in a manner that enforces a certain minimum heart rate. Pacemakers can enforce a minimum heart rate either asynchronously or synchronously. In asynchronous pacing, the heart is paced at a fixed rate irrespective of intrinsic cardiac activity. There is thus a risk with asynchronous pacing that a pacing pulse will be delivered coincident with an intrinsic beat and during the heart's vulnerable period which may cause fibrillation. Most pacemakers for treating bradycardia today are therefore programmed to operate synchronously in a so-called demand mode where sensed cardiac events occurring within a defined interval either trigger or inhibit a pacing pulse. Inhibited demand pacing modes utilize escape intervals to control pacing in accordance with sensed intrinsic activity. In an inhibited demand mode, a pacing pulse is delivered to a heart chamber during a cardiac cycle only after expiration of a defined escape interval during which no intrinsic beat by the chamber is detected. If an intrinsic beat occurs during this interval, the heart is thus allowed to "escape" from pacing by the pacemaker. When the intrinsic cardiac rhythm is such that escape beats occur, the device senses intrinsic beats through its sensing channels.

In response to the detection of a tachyarrhythmia, the device may pace in the heart with an anti-tachycardia pacing (ATP) mode. In ATP, the heart is competitively paced with one or more pacing pulses in an effort to interrupt reentrant circuits causing the tachyarrhythmia. Generally, only cardioversion/defibrillation will terminate fibrillation and certain high rate tachyarrhythmias, while ATP can be used to treat lower rate tachyarrhythmias. A rate-based criterion may thus be used by the device to decide whether to deliver ATP therapy or a defibrillation shock.

Cardiac resynchronization therapy is pacing stimulation applied to one or more heart chambers in a manner that restores or maintains synchronized contractions of the atria and/or ventricles. Certain heart failure patients suffer from interventricular and/or intraventricular conduction defects that cause the ventricles to beat in an uncoordinated manner. Ventricular resynchronization pacing is useful in treating these patients because, although not directly ionotropic, resynchronization results in a more coordinated contraction of the ventricles with improved pumping efficiency and increased cardiac output. Resynchronization pacing of the atria may also be beneficial in some heart failure patients, particularly for preventing the onset of atrial arrhythmias. One way to deliver resynchronization therapy is to pace a site with a synchronous bradycardia pacing mode and then deliver one or more resynchronization paces to one or more additional pacing sites in a defined time relation to one or more selected sensing and pacing events that either reset escape intervals or trigger paces in the bradycardia pacing mode.

3. Data Analysis for Event Prediction

An implantable cardiac rhythm management device with cardiac sensing channels such as that illustrated in FIG. 1 senses the intrinsic cardiac rhythm of the patient during periods when no pacing or other cardiac stimulation is being delivered. That information can not only be used in conjunction with delivering therapy, such as the triggering of ATP pacing or a cardioversion/defibrillation shock upon detection of an arrhythmia, but it can also be stored for later use by a clinician. An electrogram signal from a channel, for example, can be recorded in memory and later transmitted via the telemetry link to an external programmer or other device. Other information can also be recorded such as time intervals between detected sense signals, and data acquired from other types of sensing channels such as those for sensing transthoracic impedance in order to measure respiration.

Data recorded from sensing channels can also be analyzed by the device in order to predict the occurrence of pathological conditions such as arrhythmias. In a particular scheme for doing this, an arrhythmia is predicted by: 1) detecting a conditioning event statistically associated with the occurrence of an arrhythmia in a patient's heart; 2) computing a conditional arrhythmia probability for the conditioning event from past observations of instances in which the conditioning event occurs alone or together with an arrhythmia within a specified time period; 3) computing an estimated arrhythmia probability based upon the detected occurrence of the conditioning event; and 4) predicting the occurrence of an arrhythmia within a specified prediction time period if the estimated arrhythmia probability exceeds a specified threshold value.

Conditioning events may be broadly classified into markers and triggers. A marker event corresponds to a detected physiological state that is statistically associated with occurrence of cardiac arrhythmias, but the causal relationship between the marker and the arrhythmia is not known. A conditioning event is regarded as a trigger, on the other hand, if the event is thought to increase the risk of an arrhythmia occurring via a depolarization that serves as a source for the arrhythmia. Conditioning events may be detected on a beat-to-beat basis or over a longer time frame. Examples of conditioning events include a detected specific morphology of a waveform representing the electrical activity of the heart, a specific pattern of activation times of different areas of the heart as sensed by a plurality of electrodes, a specific sequence pattern of heartbeats with respect to time, a value of a measured physiological variable such as heart rate or blood pressure, or a statistic based upon a history of occurrences of conditioning events.

In one embodiment, the conditional arrhythmia probability is calculated as a ratio of the number of observed instances in which the conditioning event is followed by an arrhythmia within a specified basic time period, to the total number of observed instances of the conditioning event. In that case, the estimated arrhythmia probability for an arrhythmia to occur within the specified basic time period after detection of the conditioning event is simply the calculated conditional arrhythmia probability.

In another embodiment, the conditional arrhythmia probability CP is calculated by the expression:

$$CP = 1 - e^{-RT}$$

which assumes a Poisson probability distribution, where T is a measure of the specified prediction time period, and R is an estimate of the rate at which arrhythmias occur while the conditioning event is present. The rate R is a ratio of: 1) the number of instances in which the conditioning event is followed by an arrhythmia within a specified basic time period, to 2) the length of the basic time period multiplied by the total number of basic time periods in which the conditioning event is observed. The estimated arrhythmia probability for an arrhythmia to occur within the time T after detection of the conditioning event is again the conditional arrhythmia probability. Calculating the conditional arrhythmia probability in this manner allows the prediction time period T to differ from the length of the basic time period used to derive the conditional arrhythmia probability.

In another embodiment, rather than basing the estimated arrhythmia probability upon the detection of a conditioning event, a rate at which the conditioning event occurs is detected over some period of time. The estimated arrhythmia probability is then calculated as the product of an estimated probability that a conditioning event will occur times the probability of an arrhythmia occurring within specified time period given the occurrence of the conditioning event (i.e. the conditional arrhythmia probability). Thus:

$$\text{estimated arrhythmia probability} = (1 - e^{-RT})(1 - e^{-CT})$$

where T is a measure of the specified prediction time period, R is an estimate of the rate at which arrhythmias occur while the conditioning event is present, and C is an estimate of the rate at which the conditioning event occurs.

Another way of deriving a conditional arrhythmia probability, especially for trigger-types of conditioning events (although it can be used with any type of conditioning event), is to designate a particular detected trigger event as being responsible for causing a detected arrhythmia. Such culpability may be assigned based, e.g., upon the proximity in time between the trigger event and the onset of the arrhythmia, the magnitude of the detected trigger, or the frequency of occurrence of the trigger event within a specific time period prior to the onset of the arrhythmia. A conditional arrhythmia probability CP for that trigger event can then be calculated as a ratio of the number of instances in which the trigger event was deemed culpable for causing an arrhythmia, to the total number of occurrences of the trigger event. Also, as above, rather than basing the estimated arrhythmia probability upon the detection of the trigger event, a rate at which the trigger event occurs can be detected over some period of time. The estimated arrhythmia probability is then calculated as the product of an estimated probability that a trigger event will occur times the probability CP of an arrhythmia occurring within a specified time period T given the occurrence of the trigger event. Thus:

$$\text{estimated arrhythmia probability} = CP \times (1 - e^{-CT})$$

In another embodiment, the prediction of arrhythmias is based upon a plurality of the same or different detected conditioning events. A composite estimated arrhythmia probability is then computed as a combination of the estimated arrhythmia probabilities derived for each separately detected conditioning event. The separately detected conditioning events may be separate occurrences of the same or different conditioning events. As before, the composite arrhythmia probability is compared with a threshold value in order to predict the occurrence of an arrhythmia. In one embodiment, the composite arrhythmia probability is calculated by adding the individual estimated arrhythmia probabilities derived for each detected conditioning event, which thus assumes each individual arrhythmia probability to correspond to an independent event. In other embodiments, specific combinations of detected conditioning events are mapped in a non-linear fashion to estimated arrhythmia probabilities that can be added or otherwise combined with other estimated arrhythmia probabilities to give a composite value. In still other embodiments, the estimated arrhythmia probability is computed from a combination of conditional arrhythmia probabilities derived using different basic time periods but for the same prediction time period.

The past observations of the occurrences of conditioning events and arrhythmias from which the conditional arrhythmia probabilities are derived can be taken from either population data or from data collected in real-time from a particular patient. In a preferred embodiment, the conditional arrhythmia probabilities are based initially upon past observations of the occurrences of events and arrhythmias taken from population data, and each probability is subsequently updated from a previous value to a present value with observations taken in real-time from a particular patient. In one embodiment, a conditional arrhythmia probability is updated only if the present value differs by a predetermined amount from the previous value. In another embodiment, the amount by which the present value differs from the previous value is tested for statistical significance before a conditional arrhythmia probability is updated. In another embodiment, the previous value of the conditional arrhythmia probability is incremented or decremented by a specific amount after a prediction time period in accordance with whether the arrhythmia occurred or not, respectively.

In still another embodiment, the statistical association between the conditioning event and the occurrence of an arrhythmia is periodically reevaluated using the most recent patient-specific data. If the statistical association (e.g., as calculated from a chi-square test) is found to be below a specified value, the use of that conditional arrhythmia probability in deriving a composite estimated arrhythmia probability is discontinued.

4. Triggered Diagnostic Mode

Computational power is limited in implantable medical devices due to a finite battery supply, and it is not practical for such a device to be always performing all of the data analysis that it may be capable of. A diagnostic mode may therefore be defined where such computationally intensive data analysis as described above is performed and which may further include acquisition of additional data from the sensing channels of the device such as high fidelity electrograms for morphology analysis, accelerometer data relating to myocardial contractility or pulse pressure, and transthoracic impedance data relating to respiration patterns and onset of pulmonary edema. It would be beneficial if the device could efficiently detect when conditions are such that the probability of an arrhythmia is increased so that a deeper analysis of the collected data by the diagnostic mode is warranted. Detection of such a condition would then trigger the diagnostic mode in the device where computationally intensive data analysis is performed for predictive purposes.

Increased activity of the sympathetic nervous system, for example, is associated with metabolic stress and may predispose a susceptible patient to the onset of a cardiac arrhythmia. One means by which increased sympathetic activity may be detected is via spectral analysis of heart rate variability. Heart rate variability refers to the variability of the time intervals between successive heart beats during a sinus rhythm and is primarily due to the interaction between the sympathetic and parasympathetic arms of the autonomic nervous system. Spectral analysis of heart rate variability involves decomposing a signal representing successive beat-to-beat intervals into separate components representing the amplitude of the signal at different oscillation frequencies. It has been found that the amount of signal power in a low frequency (LF) band ranging from 0.04 to 0.15 Hz is influenced by the levels of activity of both the sympathetic and parasympathetic nervous systems, while the amount of signal power in a high frequency band (HF) ranging from 0.15 to 0.40 Hz is primarily a function of parasympathetic activity. The ratio of the signal powers, designated as the LF/HF ratio, is thus a good indicator of the state of autonomic balance, with a high LF/HF ratio indicating increased sympathetic activity. By monitoring the LF/HF ratio and initiating computation intensive data analysis for arrhythmia prediction when it exceeds a specified threshold value, the device is able to apply its computational power when it is most needed.

A cardiac rhythm management device can be programmed to determine the LF/HF ratio by analyzing data received from its ventricular sensing channels. The intervals between successive ventricular senses, referred to as RR intervals, can be measured and collected for a period of time or a specified number of beats. In order to derive a signal representing heart rate variability during a sinus rhythm, ectopic ventricular beats (i.e., premature ventricular contractions or PVCs) can be detected by monitoring whether a P wave precedes each R wave, with the RR intervals before and after the PVC changed to an interpolated or otherwise filtered value. The resulting series of RR interval values is then stored as a discrete signal. The signal can be used directly as indexed by heartbeat such that each value of the signal represents an RR interval for a particular heartbeat. Preferably, however, the signal is resampled at a specified sampling frequency in order to equalize the time intervals between signal values and thus convert the signal into a discrete time signal, where the sampling frequency is selected to meet the Nyquist criterion with respect to the frequencies of interest. In any case, the RR interval signal can then be analyzed to determine its energies in the high and low frequency bands as described above.

Figure 2:
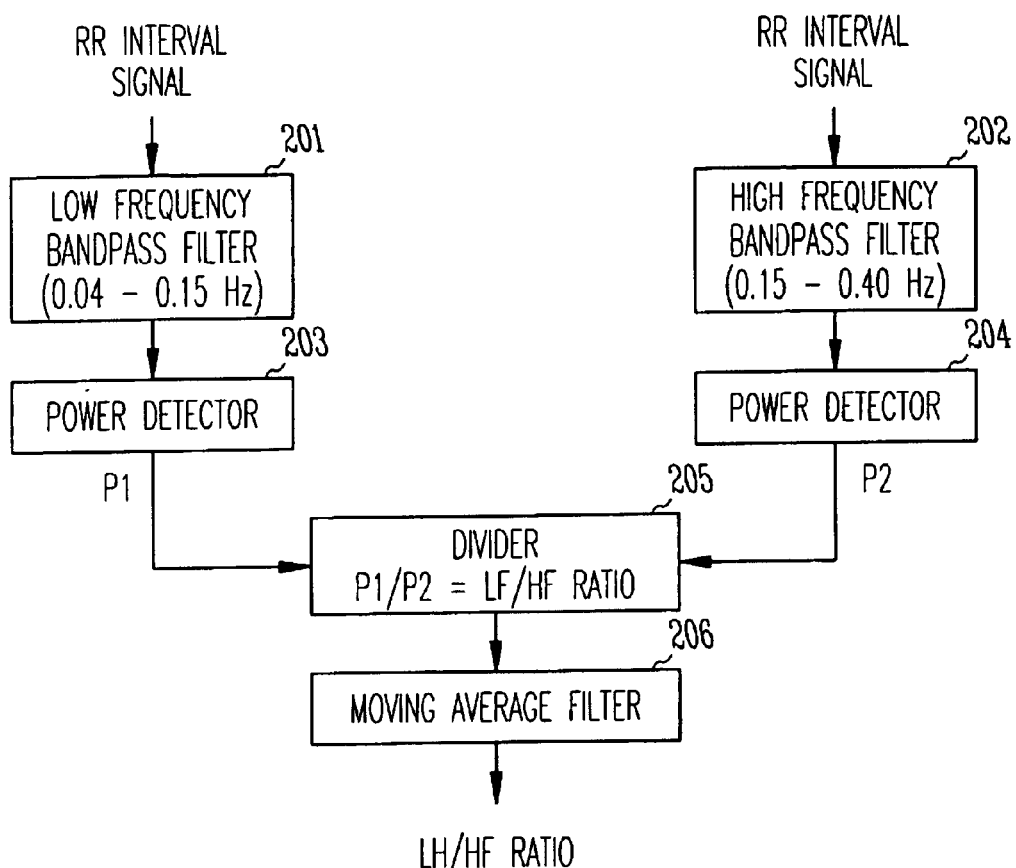
FIG. 2 is a block diagram of exemplary components for computing the LF/HF ratio.

Spectral analysis of an RR interval signal can be performed directly in the frequency domain using discrete Fourier transform or autoregression techniques. Frequency domain analysis is computationally intensive, however, and may not be practical in an implantable device. A time-domain technique for determining the high and low frequency components of the signal is therefore preferably used. FIG. 2 illustrates the functional components of an exemplary system for doing this that can be implemented as code executed by the controller and/or dedicated hardware components. The RR interval signal obtained as described above is input to both a low band digital filter 201 and a high band digital filter 202. The low band filter 201 is a bandpass filter with a passband corresponding to the LF band (e.g., 0.04 to 0.15 Hz), while the high band filter 202 is a bandpass filter with a passband corresponding to the HF band (e.g., 0.15 to 0.40 Hz). The outputs of filters 201 and 202 are then input to power detectors 203 and 204, respectively, in order to derive signals proportional to the power of the RR interval signal in each of the LF and HF bands. Power detection may be performed, for example, by squaring the amplitude of the signal and integrating over a specified average time. The output of power detector 203 is thus a signal P1 that represents the power of the RR interval signal in the LF band, and the output of power detector 204 is a signal P2 representing the power in the HF band. The signals P1 and P2 are next input to a divider 205 that computes the quantity S1/S2 which equals the LF/HF ratio. The LF/HF ratio is then input to a moving average filter 206 that computes an average value for the ratio over a specified period (e.g., 5 minutes). An updated LF/HF ratio may be computed in this manner on a beat-to-beat basis.

A diagnostic mode may thus be triggered in the device when the computed LF/HF ratio exceeds a predetermined threshold value. The predetermined threshold value may be fixed or may be determined by the device based upon previous measurements. For example, the LF/HF threshold may be set to 50% of the maximum computed LF/HF ratio value during the previous day. Additional specificity to the criteria for entering the diagnostic mode may be obtained by requiring the detected ventricular ectopic beat density to also exceed a predetermined threshold before triggering the diagnostic mode. The ventricular ectopic beat density may be measured using only interval data by defining it to be the fraction of detected R waves during a period of time that are not preceded by a P wave. The ectopic beat density threshold may either be a fixed value or made dependent upon previous measurements. An exemplary ectopic beat density threshold would be 20% above the daily average of the previous day plus one standard deviation.

Figure 3:
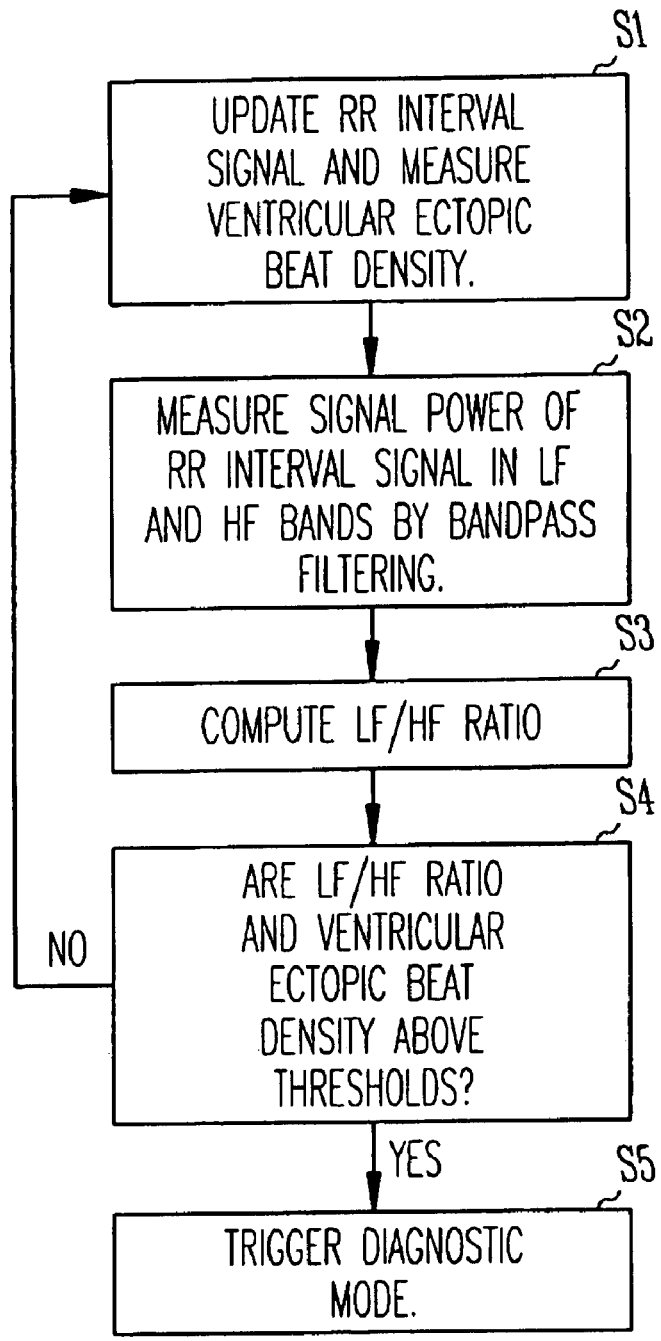
FIG. 3 is a flowchart illustrating an exemplary implementation of the triggered data storage method.

FIG. 3 is a flowchart illustrating how the controller may be programmed to implement the triggered diagnostic mode. At step S1, the RR interval signal is acquired or updated and the ventricular ectopic beat density is also calculated. At step S2, the signal power of the RR interval signal in the LF and HF bands is calculated so that the LF/HF ratio may be computed at step S3. If the LF/HF ratio and ectopic beat density are both found to be above predetermined threshold values at step S4, a diagnostic mode is triggered at step S5. As described above, the diagnostic mode is a mode in which the device performs computation intensive data analysis in order to predict future pathological events, as well as possible acquiring additional data from its sensing channels. If such data analysis results in the prediction of a pathological event with high probability, the device may then enter a prevention mode that may include the initiation of one or more therapies for preventing the occurrence of the event. Such preventive therapies may include, for example, initiation of pacing, adjustment of pacing parameters such as AV delay, reconfiguration of pacing sites, initiation of overdrive pacing, drug infusion, triggering of a patient alarm, or telemetry communication via a network of the impending event to a clinician.

Although the invention has been described in conjunction with the foregoing specific embodiment, many alternatives, variations, and modifications will be apparent to those of ordinary skill in the art. Such alternatives, variations, and modifications are intended to fall within the scope of the following appended claims.

What is claimed is:

1. A cardiac rhythm management device, comprising:
   a sensing channel for sensing ventricular electrogram signal and generating a ventricular sense (R wave) when the electrogram signal exceeds a specified threshold value;
   circuitry for measuring and collecting time intervals between successive R waves and storing the collected intervals as a discrete RR interval signal;
   bandpass filters for filtering the RR interval signal into defined high and low frequency bands;
   a power detector for determining the signal power of the RR interval signal in each of the low and high frequency bands, referred to LF and HF, respectively; and,
   circuitry for computing an LF/HF ratio and triggering a diagnostic mode if the LF/HF ratio exceeds a predetermined ratio threshold value, wherein upon entering the diagnostic mode, the device activates processing circuitry that performs data analysis to assess the probability of the occurrence of a pathological event.

2. The device of claim 1 further comprising circuitry for resampling the RR interval signal to equalize the time intervals between values of the RR interval signal.

3. The device of claim 1 further comprising circuitry for detecting ectopic ventricular beats and filtering the RR intervals before and after such beats to derive the RR interval signal.

4. The device of claim 1 further comprising:
   circuitry for detecting ectopic ventricular beats and computing an ectopic beat density as the ratio of ectopic to non-ectopic beats over a specified time period; and,
   wherein the diagnostic mode is triggered only when the ectopic beat density also exceeds a predetermined density threshold value.

5. The device of claim 4 wherein the ectopic beat density threshold is dependent upon previous measurements.

6. The device of claim 5 wherein the ectopic beat density threshold is set to approximately 20% above the daily average of the previous day plus one standard deviation.

7. The device of claim 4 further comprising circuitry for delivering an appropriate therapy when the LF/HF ratio and ectopic beat density exceed their respective predetermined threshold values.

8. The device of claim 4 further comprising circuitry for transmitting an alert signal to an external device when the LF/HF ratio and ectopic beat density exceed their respective predetermined threshold values.

9. The device of claim 1 wherein the low frequency band approximately 0.04–0.15 Hz and the high frequency band is approximately 0.15–0.40 Hz.

10. The device of claim 1 further comprising circuitry for averaging the LF/HF ratio for a specified averaging period.

11. The device of claim 1 wherein the predetermined ratio threshold value is determined by the device based upon previous measurements.

12. The device of claim 11 wherein the ratio threshold is set to approximately 50% of the maximum computed LF/HF ratio value during a previous day.

13. A method for operating a cardiac rhythm management device, comprising:
   sensing ventricular electrogram signals and generating a ventricular sense (R wave) when the electrogram signal exceeds a specified threshold value;
   measuring and collecting time intervals between successive R waves and storing the collected intervals as a discrete RR interval signal;
   filtering the RR interval signal into defined high and low frequency bands;
   determining the signal power of the RR interval signal in each of the low and high frequency bands, referred to LF and HF, respectively; and,
   computing an LF/HF ratio and triggering a diagnostic mode if the LF/HF ratio exceeds a predetermined ratio threshold value, wherein upon entering the diagnostic mode, the device activates processing circuitry that performs data analysis to assess the probability of the occurrence of a pathological event.

14. The method of claim 13 further comprising resampling the RR interval signal to equalize the time intervals between values of the RR interval signal.

15. The method of claim 13 further comprising detecting ectopic ventricular beats and filtering the RR intervals before and after such beats to derive the RR interval signal.

16. The method of claim 13 further comprising:
   detecting ectopic ventricular beats and computing an ectopic beat density as the ratio of ectopic to non-ectopic beats over a specified time period; and, triggering the diagnostic mode only when the ectopic beat density also exceeds a predetermined density threshold value.

17. The method of claim 13 wherein the low frequency band approximately 0.04–0.15 Hz and the high frequency band is approximately 0.15–0.40 Hz.

18. The method of claim 13 further comprising averaging the LF/HF ratio for a specified averaging period.

19. The method of claim 13 wherein the predetermined ratio threshold value is based upon previous measurements.

20. The method of claim 19 wherein the ratio threshold is set to approximately 50% of the maximum computed LF/HF ratio value during a previous day.

* * * * *

UNITED STATES PATENT AND TRADEMARK OFFICE
CERTIFICATE OF CORRECTION

| | |
|---|---|
| PATENT NO. | : 7,062,314 B2 |
| APPLICATION NO. | : 10/035009 |
| DATED | : June 13, 2006 |
| INVENTOR(S) | : Zhu et al. |

It is certified that error appears in the above-identified patent and that said Letters Patent is hereby corrected as shown below:

Title page, in field (63), under "Related U.S. Application Data", in column 1, line 5, delete "Mar. 8, 2001." and insert -- Mar. 8, 2001, now Pat. No. 6,678,547. --, therefor.

Title page, in field (56), under "Foreign Patent Documents", in column 2, line 1, after "5/1996" insert -- A61N 1/365 --.

Title page, in field (56), under "Foreign Patent Documents", in column 2, line 2, after "3/1994" insert -- A61B 5/0452 --.

Title page, in field (56), under "Foreign Patent Documents", in column 2, line 3, delete "4/1999" and insert -- 4/1998 --, therefor.

Title page, in field (56), under "Foreign Patent Documents", in column 2, line 3, after "4/1999" insert -- A61N 1/365 --.

Title page, in field (56), under "Foreign Patent Documents", in column 2, line 4, after "2/2000" insert -- A61N 1/368 --.

Title page, in field (56), under "Foreign Patent Documents", in column 2, line 5, after "7/2000" insert -- A61N 1/368 --.

Title page, in field (56), under "Foreign Patent Documents", in column 2, line 6, after "8/2000" insert -- A61B --.

Title page, in field (56), under "Foreign Patent Documents", in column 2, line 7, after "9/2000" insert -- A61N 1/37 --.

Title page, in field (56), under "Other Publications", in column 2, line 2, delete "Intrepretation," and insert -- Interpretation, --, therefor.

UNITED STATES PATENT AND TRADEMARK OFFICE
CERTIFICATE OF CORRECTION

PATENT NO. : 7,062,314 B2
APPLICATION NO. : 10/035009
DATED : June 13, 2006
INVENTOR(S) : Zhu et al.

It is certified that error appears in the above-identified patent and that said Letters Patent is hereby corrected as shown below:

In column 1, line 13, delete "Mar. 8, 2001," and insert -- Mar. 8, 2001, now Pat. No. 6,678,547 --, therefor.

Signed and Sealed this

Twenty-eighth Day of November, 2006

JON W. DUDAS
*Director of the United States Patent and Trademark Office*